United States Patent [19]
Cotton

[11] Patent Number: 5,546,809
[45] Date of Patent: Aug. 20, 1996

[54] VIBRATION MONITOR MOUNTING BLOCK

[75] Inventor: Harvey E. Cotton, Friendswood, Tex.

[73] Assignee: Houston Industries Incorporated, Houston, Tex.

[21] Appl. No.: 610,971

[22] Filed: Mar. 1, 1996

Related U.S. Application Data

[63] Continuation of Ser. No. 354,919, Dec. 12, 1994, abandoned.

[51] Int. Cl.⁶ ............................ G01N 29/24; G01N 29/28
[52] U.S. Cl. ................... 73/644; 73/660; 73/661
[58] Field of Search ............................. 73/644, 660, 661, 73/658, 587, 627; 310/341, 346, 348

[56] References Cited

U.S. PATENT DOCUMENTS

| | | |
|---|---|---|
| 1,895,643 | 1/1933 | Putnam . |
| 2,706,762 | 4/1955 | Alexander . |
| 2,814,742 | 11/1957 | Tognola . |
| 3,328,610 | 6/1967 | Jacke et al. ................ 73/662 |
| 3,350,923 | 11/1967 | Cross ........................... 73/644 |
| 3,555,297 | 1/1971 | Pierson ....................... 310/325 |
| 3,585,865 | 6/1971 | Bungart ...................... 73/632 |
| 3,597,962 | 8/1971 | Holtz .......................... 73/641 |
| 3,694,675 | 9/1972 | Loveday ..................... 310/325 |
| 3,934,457 | 1/1976 | Clark et al. ................ 73/637 |
| 4,270,389 | 6/1981 | Shiraiwa et al. ........... 73/622 |
| 4,393,437 | 7/1983 | Bell . |
| 4,399,485 | 8/1983 | Wright . |
| 4,408,255 | 10/1983 | Adkins . |
| 4,494,171 | 1/1985 | Bland . |
| 4,500,881 | 2/1985 | Beane . |
| 4,567,770 | 2/1986 | Rumbold et al. ........... 73/644 |
| 4,839,774 | 6/1989 | Hamburgen . |
| 4,910,642 | 3/1990 | Downing . |
| 5,034,688 | 7/1991 | Moulene . |
| 5,201,227 | 4/1993 | Iinuma et al. .............. 73/660 |

OTHER PUBLICATIONS

Webster's Third Annual New International Dictionary, 1964, pp. 1476–1477.

*Primary Examiner*—Hezron E. Williams
*Assistant Examiner*—Nashmiya Ashraf
*Attorney, Agent, or Firm*—Pravel, Hewitt, Kimball & Krieger

[57] ABSTRACT

A cooling block is provided for mounting a transducer or other electronic component on a test object which typically becomes heated during use or testing. The cooling block receives a flow of cooling gas and distributes the gas to flow outwardly past the transducer and maintain the transducer in relatively stable, constant temperature conditions. The cooling block also functions as a heat absorber. The block may be mechanically or magnetically attached to the object under test.

11 Claims, 2 Drawing Sheets

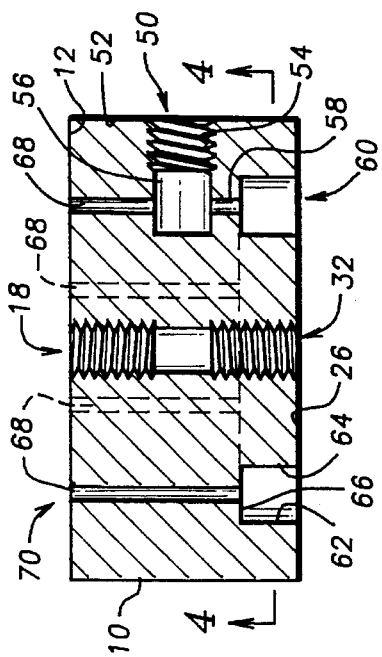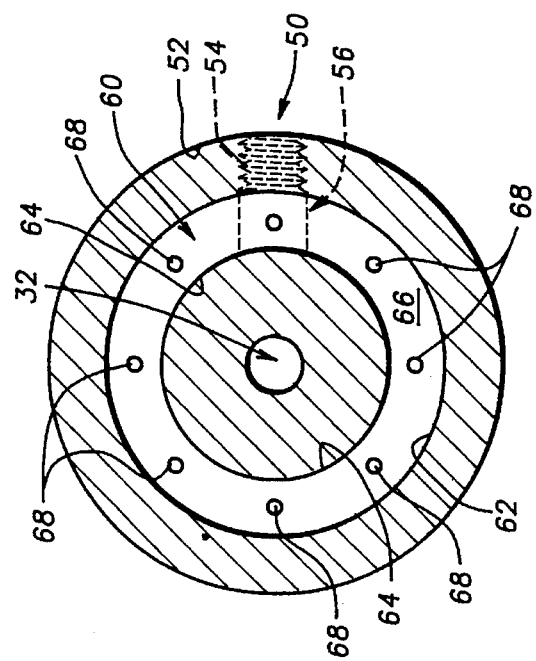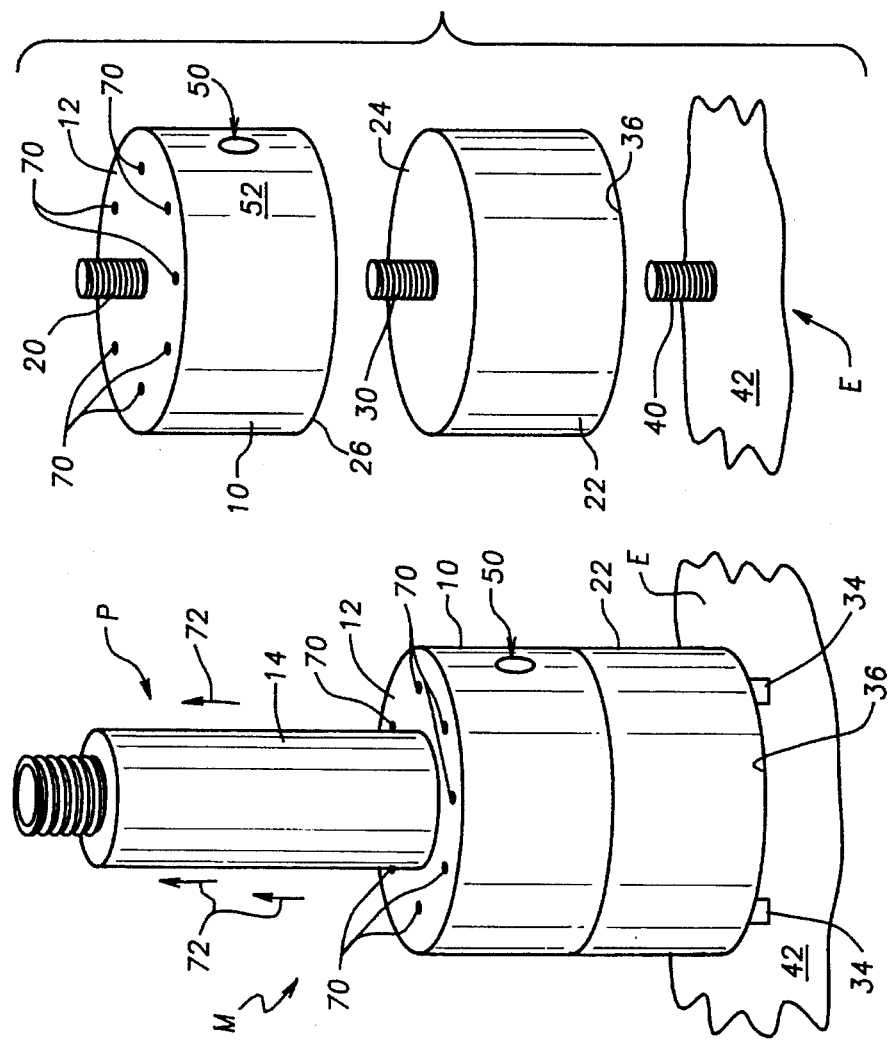

VIBRATION MONITOR MOUNTING BLOCK

This is a continuation of application Ser. No. 08/354,419 filed on Dec. 12, 1994, now abandoned.

BACKGROUND OF INVENTION

1. Field of Invention

The present invention relates to structure for mounting electrical test components on heated objects while providing cooling for the component.

2. Description of Prior Art

It has been desirable to perform vibration testing of equipment under normal service or usage conditions. To do so, it has, so far as known, been a necessary practice to mount a vibration transducer on the equipment under test for accurate readings. The transducer converted mechanical movement such as vibrations into electrical signals which were furnished to electronic test equipment or monitors.

One such type of equipment which it has been desirable to test has been turbines used in electrical power generation. When properly monitored, minor equipment problems (such as a weak or possibly loosened turbine blade) could be detected early. Once detected, the problem could be corrected before major equipment damage occurred. Typically, however, the temperature of the turbine varied under different usage conditions. As the temperature conditions of the turbine varied, the temperature of the transducer fluctuated correspondingly, causing electrical measurements signals from the transducer to also vary. Since the electrical readings from the transducer varied for reasons other than the mechanical vibrations of interest, inaccurate measurements would be furnished to the test equipment.

SUMMARY OF INVENTION

Briefly, the present invention provides a new and improved mounting block for mounting an electrical test probe such as a vibration transducer to an item of equipment for vibration testing of the equipment. The equipment is a type, such as a turbine, which becomes heated during use. The mounting block of the present invention takes the form of a block body which has a first block portion having a mounting surface formed on it for receiving the test probe. The block body also includes a second block portion which is adapted to be mounted to the test equipment. The block body may be attached to the equipment by either a magnetic mounting or a mechanical connection arrangement.

A cooling gas inlet is formed in the block body for receiving a flow of cooling gas. Flow exit passages in the form of passageways and exit ports are formed in the mounting surface of the block body to direct the cooling gas past the test probe in order to cool it. A manifold is formed in the block body distributing the cool gas from the cooling gas inlet to the flow exit passages for cooling of the test probe.

BRIEF DESCRIPTION OF THE DRAWINGS

FIG. 1 is an elevation view of a mounting block according to the present invention for a transducer on a test object.

FIG. 2 is an exploded isometric view of the mounting block of FIG. 1.

FIG. 3 is a cross-sectional view of an upper portion of the mounting block of FIG. 1.

FIG. 4 is a cross-sectional view taken along the lines 4—4 of FIG. 3.

DESCRIPTION OF PREFERRED EMBODIMENT

Figure 6:
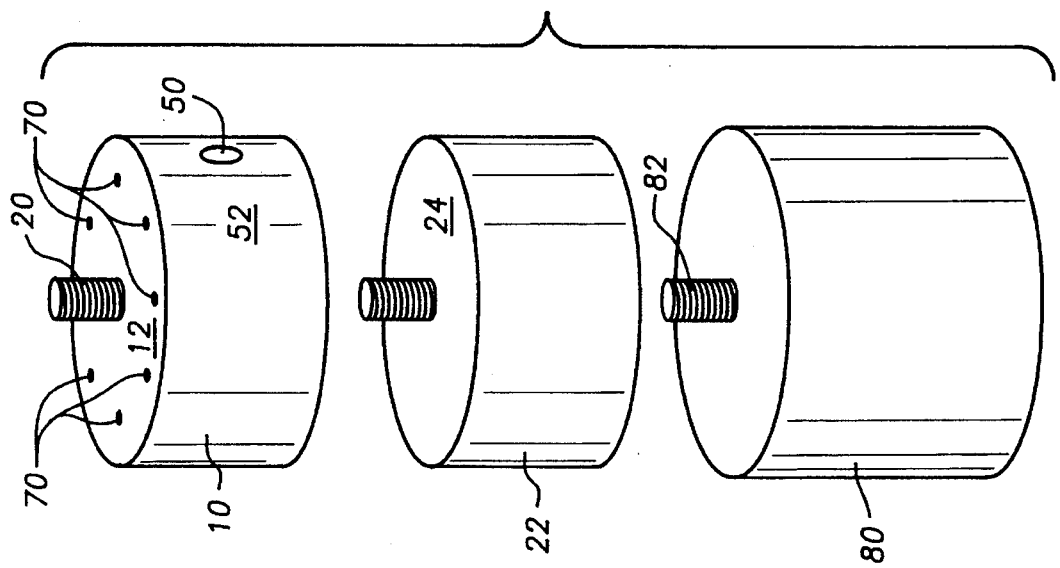
FIG. 6 is an exploded isometric view of an alternative embodiment of the mounting block of the present invention.

In the drawings, the letter M indicates generally a mounting block according to the present invention for mounting an electrical test probe P such as a vibration transducer on an item of equipment E. The transducer may be of any suitable type for electrical testing of equipment such as a vibration transducer of either the accelerometer type or the velocity probe type.

The equipment being tested may be any item or type of equipment which it is desirable to test for vibration, particularly of the type which becomes heated during operation or use. One example of such a type of equipment is a turbine used in electrical power generation. It should be understood, however, that the mounting block according to the present invention can be used with other types of equipment, as well.

Considering the mounting block M more in detail, a block body B includes a first or upper generally cylindrical block portion or member 10 made preferably from aluminum or an aluminum alloy such as 6061. The block member 10 has a mounting surface 12 formed on it for receiving the transducer or test probe P. Typically, the test probe P is enclosed within a protective housing 14 having a threaded rear connection 16 to which an electrical connector cable for the transducer P is attached for carrying signals obtained by the transducer to test instrumentation.

A threaded socket or passage 18 (FIG. 3) is formed extending inwardly into the mounting surface 12 of the block member 10. The socket 18 is adapted to receive and engage a threaded screw or other connector member 20 (FIG. 2) which extends upwardly from surface 12 to be received in a similar threaded socket in the housing 14. In this manner the transducer P is fixedly mounted to the mounting block M.

The block body B also includes a second or lower generally cylindrical block member or portion 22 which is adapted to be mounted on the turbine or equipment E. The second block member 22 is also, like block member 10, preferably formed from aluminum or an aluminum alloy. The lower block member 22 is thus formed of a heat absorbing material of suitable heat absorbing properties and functions in effect at least in part as a heat sink. This provides further protection to the test probe P from the heated equipment E.

Figure 5:
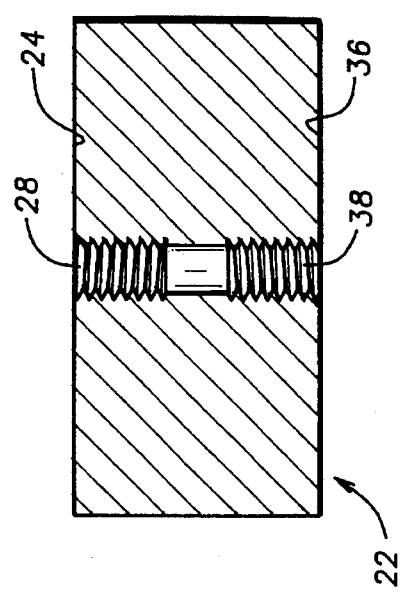
FIG. 5 is a cross-sectional view of a lower portion of the mounting block of FIG. 1.

The lower block portion 22 has an upper surface 24 adapted to be fitted against a lower surface 26 of the first block member 10. A threaded socket or passage 28 (FIG. 5) is formed extending inwardly into the upper surface 24 of the block member 22 for receipt and engagement of with a threaded screw or other connector 30 (FIG. 2). The connector 30 is also fitted into a threaded socket or passage 32 (FIG. 3) in the lower surface 26 of the block member 10 in order to connect the block members 10 and 22 of block body B together.

The lower block member 22 may be attached to the equipment E magnetically by magnets 34 (FIG. 1) mounted on a lower surface portion 36. Alternatively, the mass of the block member 22 may be formed at least in part from some suitable conventional magnetic material. The lower block member 22 may also be mechanically connected to the equipment E being tested. In this situation, a threaded socket or passage 38 (FIG. 5) is formed extending inwardly into the lower surface 36 of the block member 22 so that a threaded screw or connector member 40 (FIG. 2) extending from a surface 42 of the equipment E may be inserted. In this way, the block body B may be mechanically connected with the equipment E under test.

Considering the block member 10, a cooling gas inlet 50 is formed extending into a side wall 52 of the block member 10 of the block body B adjacent a threaded surface 54. The threaded surface 54 is adapted to engage and receive a threaded connector end of a supply hose or tube which conveys a cooling gas, such as air or nitrogen, to the mounting block M. The pressure, temperature and flow rate of the incoming cooling gas is selected based on heat control requirements. Air at ambient temperature and pressures in the range of from about 10 to about 90 psig has proven satisfactory.

An inlet chamber 56 is formed in the block body B inwardly of the cooling gas inlet 50 and is connected by a passage or port 58 to a generally toroidal air slot or duct 60. The air duct 60 is formed extending inwardly from the lower surface 26 of block member 10. The air duct 60 is defined by cylindrical side walls 62 and 64, extending generally perpendicularly to the lower surface 26, and a top wall or roof 66 in the block member 10. The air slot or duct 60 is sealed against substantial gas leakage when body members 10 and 22 of the body block B are connected together. If desired, O-rings or other suitable seals may be installed between body members 10 and 22 in suitable slots or grooves adjacent the air duct 60.

The air duct 60 functions as a manifold in the mounting block M, distributing the cooling gas received at the inlet 50 and chamber 56 to a number of flow exit passages 68. The flow exit passages 68 are formed extending upwardly from the top wall 66 in the block member 10 to cooling outlet ports 70 formed in the upper or mounting surface 12. The passages 68 and outlet ports 70 function to direct the cooling gas received from air duct 60 upwardly in flow paths indicated by arrows 72 past the test probe P. The upwardly flowing cooling gas serves to maintain the test probe P in substantially isothermal conditions as the equipment E being tested becomes heated during operation.

In the embodiment illustrated, eight equally spaced flow passages 68 spaced at 45° intervals from adjacent passages are formed in the block member 10. It should be understood, however, that other numbers and spacings of flow exit passages and ports may be used, depending on cooling requirements.

In some situations, it may be desirable to provide additional heat protection for the test probe from the equipment E. In those instances, a cylindrical lug blind or block 80 (FIG. 6) of heat absorbing material may be mounted between the block member 22 and the equipment E, either magnetically, or mechanically as shown by a threaded connector 82. Alternatively, the block 80 may be mounted between the block members 10 and 22. The block 80 is formed of a mass of heat absorbing material, such as that of lower block member 22. The block 80 thus provides an additional heat absorbing mass to further protect the test probe P.

Having described the invention above, various modifications of the techniques, procedures, material and equipment will be apparent to those in the art. It is intended that all such variations within the scope and spirit of the appended claims be embraced thereby.

I claim:

1. A mounting block structure for mounting an electrical test probe for vibration testing of equipment which becomes heated during use, comprising:

a block body, said block body comprising:
a first block member having a mounting surface thereon for receiving the vibration test probe to extend outwardly therefrom;
a second block member adapted to be mounted to the equipment;

means for interconnecting said first and second block members to form said block body:

means with said second block member for mounting said block body to the equipment;

a cooling gas inlet formed in said first; block member of said block body on a surface other than said mounting, said surface inlet for receiving a supply of cooling gas;

flow exit passages formed in said mounting surface of said first block member for directing the cooling gas outwardly from said mounting surface past the test probe to cool the test probe;

manifold means comprising a fluid flow duct formed inwardly of said cooling gas inlet in said first block member of said block body for distributing the cooling gas from said inlet to said flow exit passages for cooling of the test probe; and said flow exit passages being formed in said first block member extending from said fluid flow duct of said manifold means through said mounting surface for passage of the cooling gas to cool the vibration test probe.

2. The structure of claim 1, wherein said means for mounting comprises:

means for magnetically mounting said block body on the equipment.

3. The structure of claim 1, wherein said means for mounting comprises:

means for mechanically connecting said block body with the equipment.

4. The structure of claim 1, wherein:

said manifold means is formed in a lower surface of said first block member opposite said mounting surface.

5. The structure of claim 1, wherein:

said flow exit passages comprise a plurality of uniformly spaced gas flow passages formed in said first block member between said manifold means and said mounting surface.

6. The structure of claim 1, wherein:

said second block member comprises a mass of heat absorbing material,

7. The structure of claim 1, wherein the electrical test probe comprises a vibration transducer.

8. The structure of claim 1, wherein the equipment comprises a turbine.

9. The mounting block of claim 1, wherein said flow exit passages direct said cooling gas past the test probe after said cooling gas has left said flow exit passages.

10. The mounting block of claim 1, wherein said flow exit passages direct said cooling gas into contact with the test probe.

11. A mounting block for mounting a vibration transducer to a turbine which becomes heated during testing thereof, comprising:

a block body, said block body comprising:
- a first block member having a mounting surface thereon for receiving the vibration transducer to extend outwardly therefrom;
- a second block member adapted to be mounted to the turbine;

means for interconnecting said first and second block members to form said block body;

means with said second block member for mounting said block body to the turbine;

a cooling gas inlet formed in said first block member of said block body on a surface other than said mounting surface, said inlet for receiving a supply of cooling gas;

flow exit passages formed in said mounting surface Of said first block member for directing the cooling gas outwardly from said mounting surface past the vibration transducer to cool the vibration transducer;

manifold means comprising a fluid flow duct formed inwardly of said cooling gas inlet in said first block member Of said block body for distributing the cooling gas from said inlet to said flow exit passages for cooling of the vibration transducer; and said flow exit passages being formed in said first block member extending from said fluid flow duct of said manifold means through said mounting surface for passage of the cooling gas to cool the vibration transducer.

* * * * *